US012592297B2

(12) United States Patent
Zeni et al.

(10) Patent No.: US 12,592,297 B2
(45) Date of Patent: Mar. 31, 2026

(54) METHOD OF ALIGNING STRINGS OF CHARACTERS REPRESENTING GENOMIC DATA AND RELATED HARDWARE DEVICE

(71) Applicant: HUXELERATE S.R.L., Milan (IT)

(72) Inventors: Alberto Zeni, Pizzighettone (IT); Matteo Crespi, San Giuliano Milanese (IT); Lorenzo Di Tucci, Peschiera Borromeo (IT); Marco Domenico Santambrogio, Cinisello Balsamo (IT); Fabio Pizzato, Milan (IT)

(73) Assignee: HUXELERATE S.R.L., Milan (IT)

( * ) Notice: Subject to any disclaimer, the term of this patent is extended or adjusted under 35 U.S.C. 154(b) by 1166 days.

(21) Appl. No.: 17/594,585

(22) PCT Filed: Apr. 23, 2020

(86) PCT No.: PCT/IB2020/053846
§ 371 (c)(1),
(2) Date: Oct. 22, 2021

(87) PCT Pub. No.: WO2020/217200
PCT Pub. Date: Oct. 29, 2020

(65) Prior Publication Data
US 2022/0108770 A1 Apr. 7, 2022

(30) Foreign Application Priority Data
Apr. 23, 2019 (IT) ........................ 102019000006232

(51) Int. Cl.
G16B 30/10 (2019.01)
G06F 16/901 (2019.01)
(Continued)

(52) U.S. Cl.
CPC .......... *G16B 30/10* (2019.02); *G06F 16/901* (2019.01); *G06N 3/126* (2013.01); *G16B 30/20* (2019.02)

(58) Field of Classification Search
None
See application file for complete search history.

(56) References Cited

U.S. PATENT DOCUMENTS

2008/0086274 A1 4/2008 Chamberlain et al.

FOREIGN PATENT DOCUMENTS

WO WO-2020217200 A1 10/2020

OTHER PUBLICATIONS

Dandass, Yoginder S., et al. "Accelerating string set matching in FPGA hardware for bioinformatics research." BMC bioinformatics 9 (2008): 1-11. (Year: 2008).*

(Continued)

*Primary Examiner* — Karlheinz R. Skowronek
*Assistant Examiner* — Mary C Leverett
(74) *Attorney, Agent, or Firm* — STERNE, KESSLER, GOLDSTEIN & FOX P.L.L.C.

(57) ABSTRACT

A method of aligning a first string (read) of characters representing genomic data to a second string (contig) of characters representing genomic data, using at least a Finite State Machine having a storage memory, is disclosed. Substantially, data representing at least a first string of characters representing genomic data (read) and at least a second string of characters representing genomic data (contig) are loaded into a storage memory and a first block of characters of the read and a second block of characters of the contig are selected, wherein the two blocks have the same number of characters and are identified respectively by a first index and (Continued)

by a second index pointing to start positions of the two blocks. Then the two blocks of characters are compared and the two indexes are updated at each cycle of the Finite State Machine until all blocks of characters of the read have been compared. It is also disclosed a hardware device, preferably a FPGA, configured for executing the disclosed method.

7 Claims, 11 Drawing Sheets

(51) Int. Cl.
| | | |
|---|---|---|
| *G06N 3/126* | (2023.01) | |
| *G16B 30/20* | (2019.01) | |

(56) References Cited

OTHER PUBLICATIONS

Kim, HyunJin, and Kang-Il Choi. "A pipelined non-deterministic finite automaton-based string matching scheme using merged state transitions in an FPGA." PloS one 11.10 (2016): e0163535. (Year: 2016).*

Fernandez, Edward B., et al. "FHAST: FPGA-based acceleration of Bowtie in hardware." IEEE/ACM transactions on computational biology and bioinformatics 12.5 (2015): 973-981. (Year: 2015).*

Bekbolat, M., et al., "HBLast: An Open-Source FPGA Library for DNA Sequencing Acceleration," 2019 IEEE International Parallel and Distributed Processing Symposium Workshops (IPDPSW), pp. 79-82, Institute of Electrical and Electronics Engineers, United States (May 2019).

Fernandez, E., et al., "String Matching in Hardware Using the FM-Index," 2011 IEEE 19th Annual International Symposium on Field-Programmable Custom Computing Machines, pp. 218-225, Institute of Electrical and Electronics Engineers, United States (May 2011).

Guyetant, S., et al., "Cluster of re-configurable nodes for scanning large genomic banks," *Parallel Computing 31*(1):73-96, Elsevier, Netherlands (Jan. 2005).

International Search Report and Written Opinion for International Application No. PCT/IB2020/053846, European Patent Office, Netherlands, mailed on Jul. 6, 2020, 16 pages.

Zeni, A., et al., "An FPGA-Based Computing Infrastructure Tailored to Efficiently Scaffold Genome Sequences," 2019 IEEE 27th Annual International Symposium on Field-Programmable Custom Computing Machines (FCCM), p. 333, Institute of Electrical and Electronics Engineers, United States (Apr. 2019).

* cited by examiner

METHOD OF ALIGNING STRINGS OF CHARACTERS REPRESENTING GENOMIC DATA AND RELATED HARDWARE DEVICE

TECHNICAL FIELD

This disclosure relates to techniques for aligning genomic data and more particularly to a method, implemented through a Finite State Machine, of aligning strings of characters representing genomic data and a related hardware device configured to implement the method.

BACKGROUND

The science of molecular biology has progressed rapidly to the point where characterization and sequencing of the entire genome of an organism is feasible. However, at the present time, the characterization and sequencing of large genomes requires the sequencing of each region of the genome multiple times in order to obtain a complete, contiguous sequence.

Currently, several strategies are available for sequencing large genomes. This is done by aligning and merging fragments from a longer DNA sequence in order to reconstruct the original sequence. This is needed as DNA sequencing technology cannot read whole genomes in one go, but rather reads small pieces of bases, depending on the technology used. Typically the short fragments, called reads, result from shotgun sequencing genomic DNA, or gene transcript (ESTs).

In the shotgun sequencing method, the genome is randomly fragmented and cloned into sequencing vectors. The resulting clones are sequenced and overlapping sequences are identified and ordered to generate a contiguous sequence. Using this approach, high quality sequence can only be assembled after very large amounts of sequence data, ranging from five to seven times the amount of raw data to be sequenced, are accumulated.

Typically, a DNA is sequenced by using sequencing machines such as the ones by Illumina [1]. However, these machines, given a sample of the DNA of the individual, do not provide the complete DNA strand. In fact, they provide small (where the dimension depends on the technology used) and repetitive fragments of the DNA strand called "reads". To produce a full DNA strand and perform the analysis on the genome, the reads need to pass through a process called genome assembly, which involves various steps to produce the original sequence. In some cases, the genome that will be analyzed is a novel one and thus there are no reference sequences available for alignment. For this reason, assembly of these genomes are called de-novo and are largely used to exploit analysis of functional genomics, gene expression and species diversity. Genome Assembly is particularly computationally intensive [2], requiring highly optimized algorithms and architectures capable of managing the huge amount of data coming from the sequencer. As of now, this issue, has been addressed developing software tools, such as SOAPDenovo2 [3], ABySS [4] and SSPACE [5]. However, general purpose hardware, on which these software are executed, is not optimized to manage the huge loads that these algorithms need to process. In these regards, a custom architecture implemented on Field Programmable Gate Array (FPGA) can offer a more efficient solution [6, 7], allowing to exploit the full parallelism of the algorithms while keeping a relatively low power profile. In this paper, we present a scalable, energy efficient, high performant architecture for the aligning step of SSPACE on FPGA.

SSPACE is the most commonly used tool for scaffolding, thanks to its accuracy and versatility, being a standalone tool. Furthermore, it exploits a very well-known software to perform exact sequence alignment called Bowtie [8], which is used and can be integrated into other genomic pipelines. The latter matches genomic sequences by first compressing genomic data using the Burrows-Wheeler Transform (BWT), and then explores the compressed data searching for alignments.

A description of an algorithm for aligning reads and contigs into "scaffolds" is provided. The concept of genome assembly, providing a detailed description of one of its steps, the scaffolding phase, is illustrated first. Then the algorithm implemented within SSPACE is described.

A. Genome Assembly

Genome assembly refers to the process of aligning and merging fragments from a longer DNA sequence to reconstruct the original DNA sequence. Indeed, to perform DNA sequencing, machines cannot read the whole genome, but only small pieces of it. DNA repetitions are produced to avoid lack of information during the sequencing. This redundancy makes the assembly of the genome and its analysis extremely complex tasks, which often requires long time-to-result due to the significant size of genomes. Genome assembly can be mainly performed in 2 ways: reference-based and de-novo. The reference-based assembly approach involves mapping genomic sequences to an already assembled genome. The goal of this process is to identify genetic variations of the new genome with respect to the existing one. De-novo genome assembly, instead, relies only on the reads coming from the sequencing machine to create full-length (sometimes novel) sequences. Genome assembly is a multistep task where we can identify four different phases (FIG. 1). The first phase of the assembly pipeline filters reads coming from the sequencer machine. This is necessary as the sequencing machine could introduce some errors in the sequences while reading the DNA sample. In the next phase, called contigging, all the filtered reads are compared to each others. The goal of this step is to identify possible overlaps among reads and creating longer reads called "contigs", which are contiguous fragments of DNA sequence from an incomplete draft genome. Reads that do not overlap are then aligned with the contigs in the scaffolding phase. The goal of this process is to search for further overlaps in the contigs to group them together into longer sequences. The last step in genome assembly is the annotation phase. In this step, the locations of genes, as well as the individual function of different DNA chunks are identified. Using a known genome, the assembly is simply performed aligning all the sequences to the reference one, but in the case of de-novo assembly this approach cannot be applied. It is necessary to compare reads to each other, and then build longer contiguous sequences using the overlapped reads. Scaffolding represents the step between the contigs creation and the gene annotation phase of genome assembly (FIG. 1). The focus of this phase is to reconstruct the genome using the sequences obtained by the contigging phase. The creation of scaffolds is exploited by aligning reads multiple times with the contigs (FIG. 2). Reads can be used to fill the various gaps between contigs or as links between different contigs to group them into larger sequences. To scaffold contigs, most commonly used algorithms rely on reordering and realigning the sequences using aligned reads as a guide to this process. These processes involve basic mathematical operations (sums, shifts and comparisons) that need to be performed multiple times to maximize the accuracy of the scaffold placement. Furthermore, the structure of the scaffolding process permits to express significant parallelism as multiple read-contig pairs can be independently evaluated in parallel. Considering the type of operations involved, the amount of parallelism that it is possible to express and previous work on sequence alignment [6, 7], a hardware architecture for this phase of genome assembly would be beneficial to reduce the overall execution time of the algorithm.

B. Algorithm Description

To create scaffolds, SSPACE relies on exact alignment of paired-end reads with the contigs. Each read is aligned to each contig to establish a relation between different sequences. When both the reads of the same pair align with two different contigs, a link between the two contigs is formed. However, if one read aligns with more than a contig, we cannot know which contigs to connect and which not. Multiple contigs cannot share the same link, as coupling them together will potentially introduce errors in the assembled genome. Therefore, reads that map multiple times on contigs are not considered for contig pairing. Contig pairs are only considered if the calculated distance between them—the distance between the aligned reads—satisfies the mean distance specified by the user. Couples of contigs that have a valid distance are grouped together and used to create longer sequences called scaffolds. All paired contigs are used to create scaffolds, if contigs have multiple links, a bigger scaffold is created if possible. The alignment in SSPACE is performed by Bowtie, a state of the art tool for genome sequence alignment. Usually Bowtie exploits Smith-Waterman, a well-known algorithm to identify the similarity between reads, for the alignment process. However, in this case, as Bowtie is used to perform exact alignment, Smith-Waterman results not to be a good candidate to provide precise results.

RELATED WORKS

In this Section, a brief overview of the state of the art regarding scaffolding as well as hardware implementations of Bowtie is presented. Several methods have been proposed for scaffold creation, mainly based on De Bruijn Graphs (DBG), Overlap Layout Consensus (OLC) and Smith-Waterman alignment. SSPACE [5] (SSAKE-based Scaffolding of Pre-Assembled Contigs after Extension) exploits the work of SSAKE [9] and performs a sequence mapping using also Bowtie [10]. Before running the scaffolding phase, SSPACE uses a filtering algorithm to avoid the use of non ACTG and low-quality bases. Then, reads are mapped among the contigs, and finally scaffolds are assembled. The quality of the scaffolds is often measured using the N50 [11], that is defined as the minimum contig length needed to cover 50% of the genome. The authors compared their results with SOAPdenovo [3], that uses a sparse DBG based approach and ABySS [4] which cannot be employed in de novo assembly because contigs are aligned over a reference genome. SSPACE is highly used for assembly purposes because of its good performances with respect to the N50 and number of contigs concatenated into scaffolds. Also, Bambus 2 [12] uses a graphbased approach to perform metagenome assembly. As previously stated, genome assembly is a computationally intensive task due to the presence of repetitive operations and huge amount of data to be processed. For this reasons hardware acceleration of assembly algorithms have been presented in recent years. GRASShopPER [13] developed an algorithm for de novo assembly based on GPU, whereas contigs creation is optimized in hardware, the scaffolding phase is performed by SSPACE and SOAPdenovo2. Fassem [14] uses DBG and OLC to manage contigs pre-processing using FPGAs and finally create scaffolds in software. A CUDA-based implementation of SSAKE is presented on [15], where the parallelization of the tool on the architecture is based on the subdivision of the DNA sequences among the CUDA threads. The work presented in FHAST [16] implements part of Bowtie on FPGA and focuses on the search of reads in the BWT tree built by Bowtie. Although they present remarkable results on this matter, the presented implementations still need the BWT structure to be built to list all the alignments. However, the majority of time required by Bowtie (99.27% of its execution time) concerns the construction of the BWT tree, hence this acceleration affects just a little portion of the overall execution time. In this paper we propose a scalable, high performance FPGA based architecture of the alignment space of SSPACE, capable to perform the alignment phase without any support structure.

The process of exploring compressed data according to the Burrows-Wheeler Transform (BWT) searching for alignments, permits to speedup the research for alignments within the sequences but presents a serious bottleneck when multiple alignments have to be performed. Indeed, every time Bowtie aligns a new set of sequences, the BWT compression step, which takes up most of the execution time of Bowtie, must be repeated.

SUMMARY

To address this problem we reorganized the structure of the alignment step to be performed directly, avoiding the need for any support structure, while still producing the same exact results as Bowtie. This implementation will permit to speedup not only SSPACE, but also all the tools that use Bowtie as core aligner in the same manner. The design has been implemented using Xilinx SDAccel and the Vivado Design Suite, and the final implementation has been benchmarked using two different Xilinx FPGAs.

The method of this disclosure, implemented through a Finite State Machine, is defined in the enclosed claim 1. Substantially, data representing at least a first string of characters representing genomic data (read) and at least a second string of characters representing genomic data (contig) are loaded into a storage memory and a first block of characters of the read and a second block of characters of the contig are selected, wherein the two blocks have the same number of characters and are identified respectively by a first index and by a second index pointing to start positions of the two blocks. Then the two blocks of characters are compared and the two indexes are updated at each cycle of the Finite State Machine until all blocks of characters of the read have been compared.

It is also disclosed a hardware device, preferably a FPGA, configured for executing the disclosed method.

DETAILED DESCRIPTION

Figure 1:
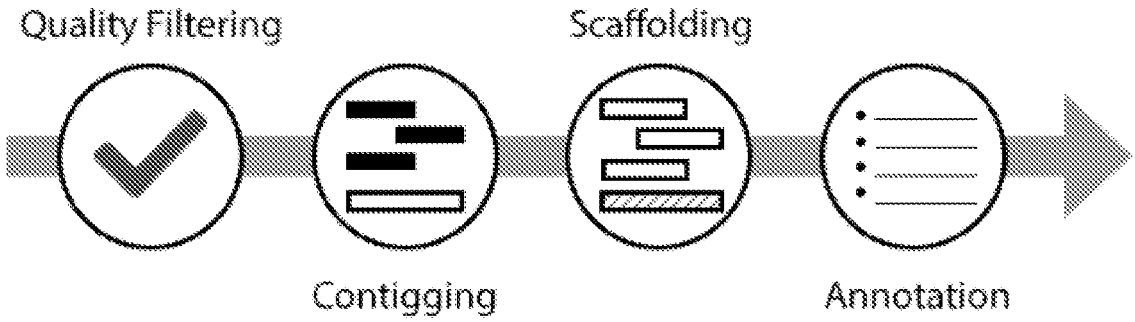
FIG. 1 illustrates a genome assembly pipeline. Firstly, a quality filter is applied to all the libraries, then contigs and scaffolds are generated. Genes expression is finally annotated and the assembly is complete.
Figure 2:
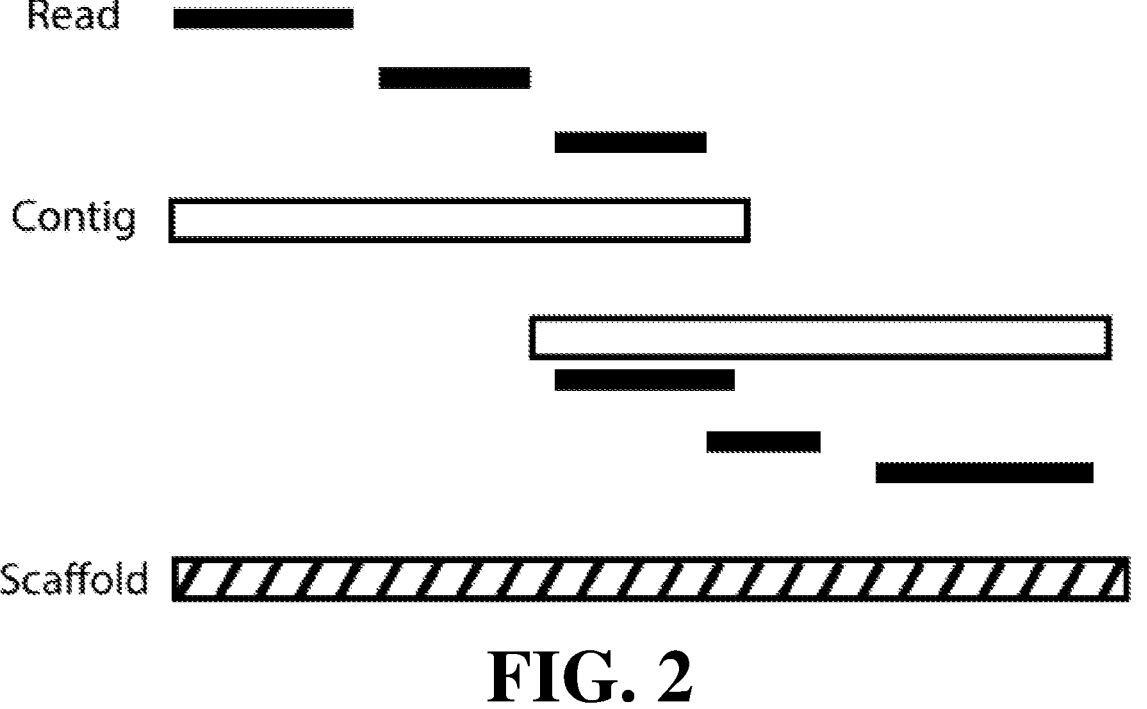
FIG. 2 illustrates a scaffolding process overview. Reads can be aligned and concatenated to create contigs. In such a similar way, contigs are merged and used for scaffold generation.

With an input of 10M contigs and 2k reads both of length 128 characters, a typical input for the tool SSPACE takes 158 minutes to complete. The 86.7% of this time, 137 minutes, is required by Bowtie to perform 2 steps: the building of the BWT tree and the final alignment. Among these two steps, the most compute intensive is the creation of the BWT, requiring almost 86.1% of the total time of SSPACE. This step involves the creation of a data structure that is then used to efficiently perform the alignment of the sequences provided as input. The problem with such data structure, is that it needs to be re-created multiple times when performing a multi-alignment. This phase represents a clear bottleneck in Bowtie; to speedup the execution of the alignment process, we reorganized and optimized the algorithm to directly compare two sequences. The architecture proposed, therefore, does not require the creation of any structure to perform the alignment.

Substantially, the aligner function keeps a read sequence stationary while it compares a series of contigs against it and then repeats this operation for every read. The string matching process compares every character of two sequences until the two sequences match or the end of one of the two is reached. Reads are usually smaller than contigs, it is not possible to skip to the next contig when two characters do not match, but rather to restart the alignment from the next contig character.

A description of the proposed hardware architecture and the method implemented thereby is given. We start with a high-level overview of its structure, followed by a detailed description of the implementation of the single core architecture. Finally, we describe how this architecture has been replicated in a multicore implementation.

A. Overview

The processor architecture is composed by three blocks, a data fetcher, a Finite State Machine (FSM) that performs the various operations on the data and, finally, a data writer. The data is uploaded from the host computer to the global memory of the FPGA.

Then, the data fetcher loads data for the FSM, which starts comparing all the sequences using a computing window able to process 128 characters per clock cycle. Once there are no sequences left, the FSM completes its execution and the data writer sends all the results back to the host.

B. Single Core

Figure 3:
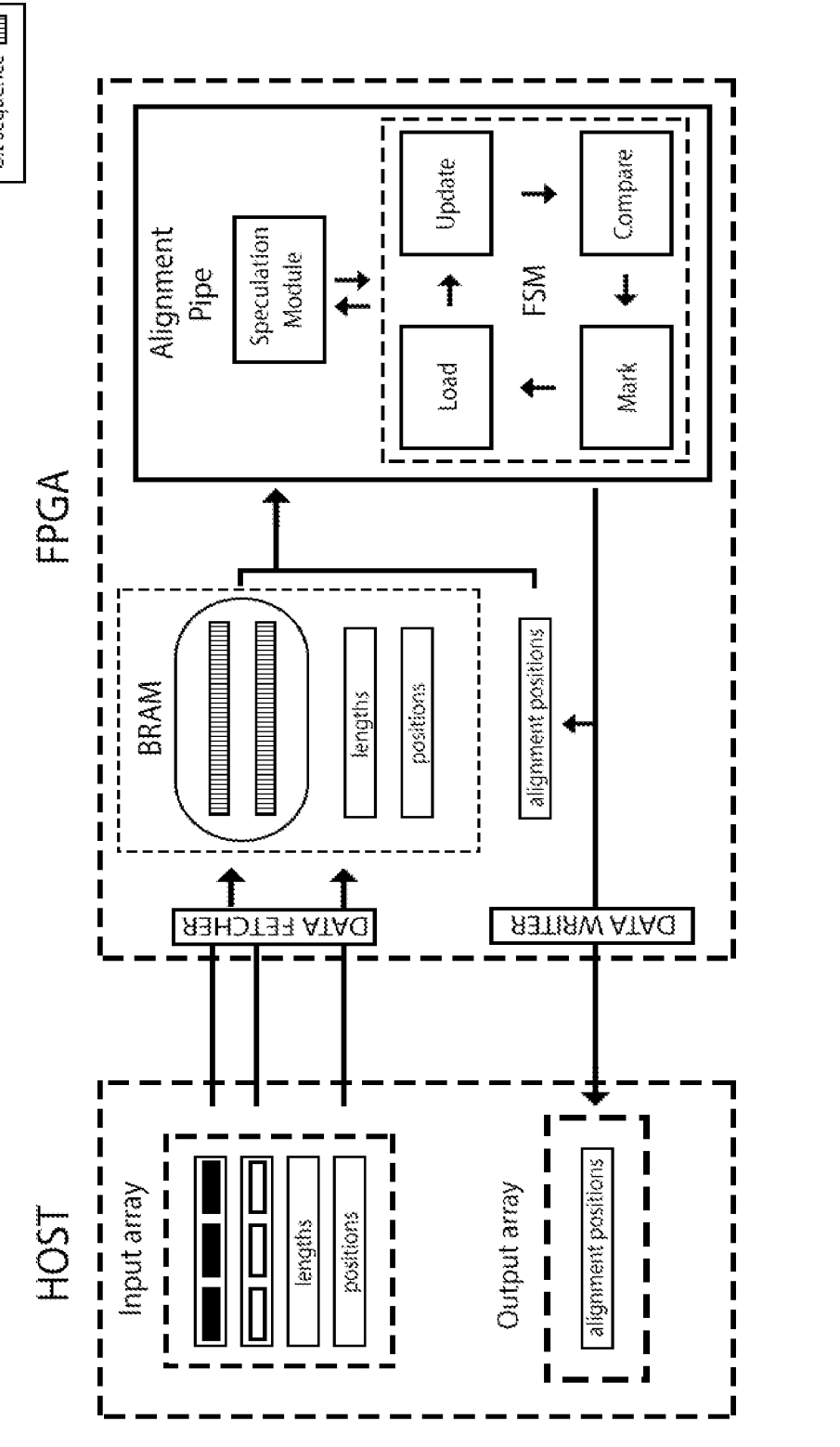
FIG. 3 illustrates a single core architecture. The input array is driven into the FPGA using the data fetcher, reads and contigs are stored in 512-bit blocks. A four-state FSM processes the data and the result is sent to the host by the data-writer.

The single core architecture, completely designed in C++, is shown in FIG. 3. The execution flow starts by loading data on the FPGA. The data fetcher loads data containing all information regarding the lengths, the number of sequences to align and the sequences themselves. To optimize data reads from the global memory and leverage the full bandwidth on the FPGA board, we set the memory ports to 512 bits, and we exploited memory burst. In this way, we are able to read 512 bits per clock cycle and per each memory port available on the FPGA. Considering that we need only 5 characters to represent our input data (A, C, G, T and N), we optimized memory transfers by representing each input character with just 4 bits. This data compression allows us also to load a 512-bit block, being sure that no character overlaps among different blocks (e.g. the first 3 bits in a block and the fourth bit in the next block). Consider that this optimization not only allows us to read more data per memory burst but also reduces the complexity of the routing and the logic circuits on the FPGA, as we would need to allocate smaller buffers. The data read is then stored on the Block RAM (BRAM) of the device to increase data locality. Two buffers have been allocated to host all the reads and contigs.

The present method will be disclosed referring to the most frequent case in which a plurality of reads is to be compared with a plurality of contigs, though the disclosed method may be applied also when a single read is to be compared with a single contig.

Figure 4:
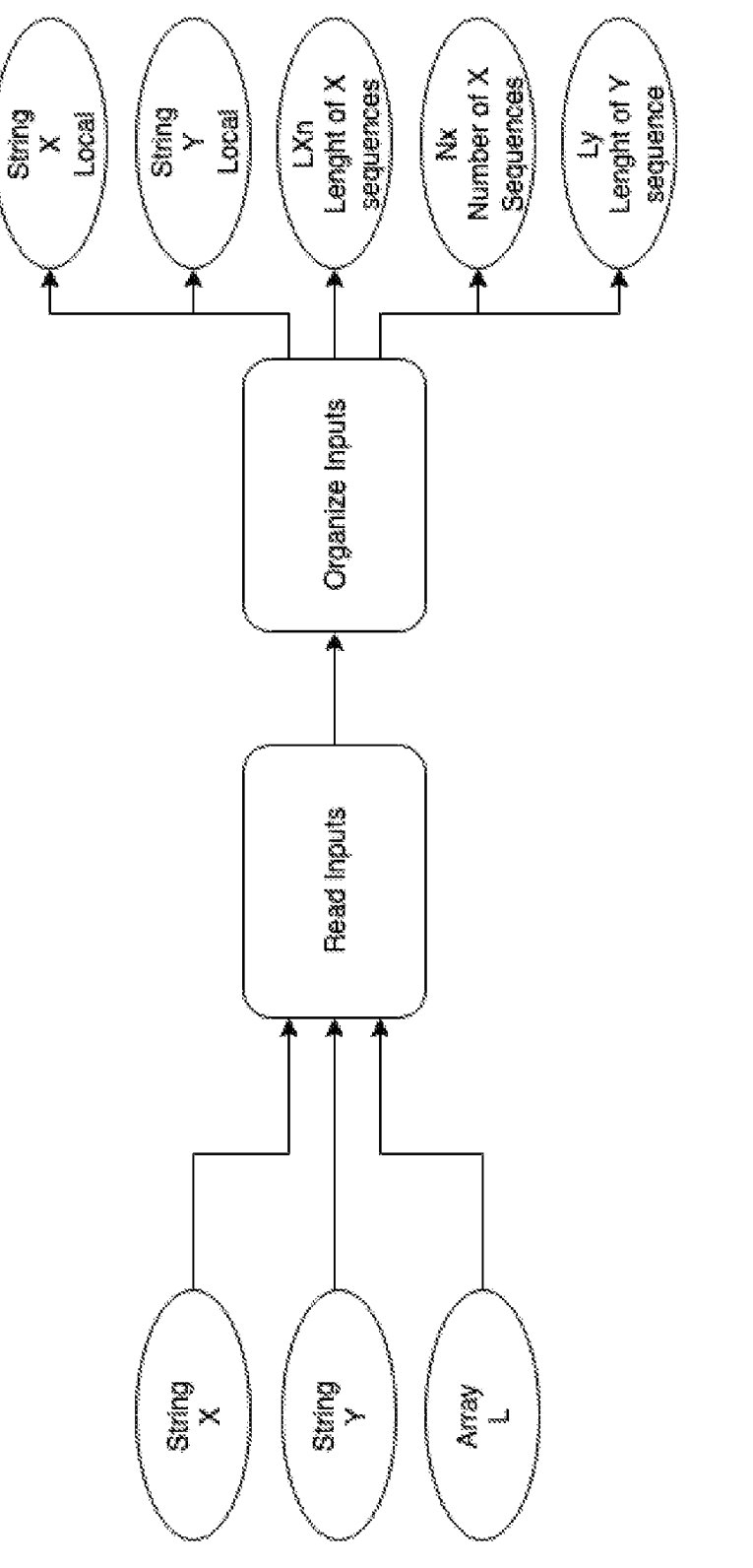
FIG. 4 schematically illustrates operations carried out for parsing input data and identifying strings to be compared.

According to an aspect of the method of this disclosure (FIG. 4), two strings of characters, namely X and Y, are loaded into a storage memory together with an array L of integers that contains the lengths LXn of the plurality of reads contained in X, the number Nx of reads, and the lengths LY of the plurality of contigs. These input data are fetched to identify a first string X_Local (read) of characters representing genomic data to be compared with a second string Y_Local (contig) of characters representing genomic data. All the data needed for the alignment are preferably stored locally to speed-up the successive stages, more preferably in different structures to simplify memory access.

Figure 5:
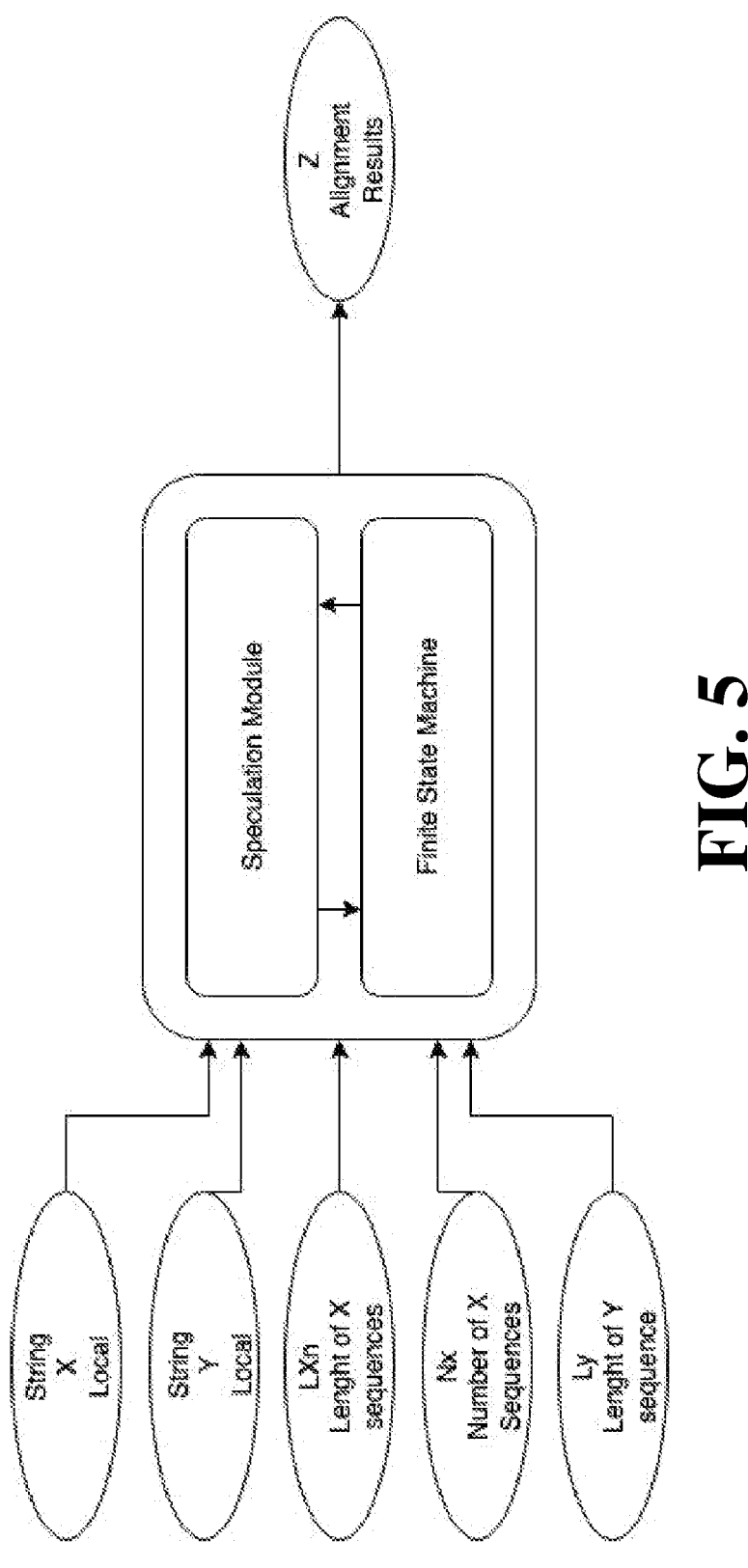
FIG. 5 schematically illustrates how results of alignment between input strings are generated.

As sketched in FIG. 5, the first string X_Local (read) of characters and the second string Y_Local (contig) of characters, together with information regarding their respective lengths, are processed by a Finite State Machine to generate an output string Z, that represent the result of the alignment between all the strings in X and the string Y. When all strings have been compared, the results can be written back to the host.

Figure 6:
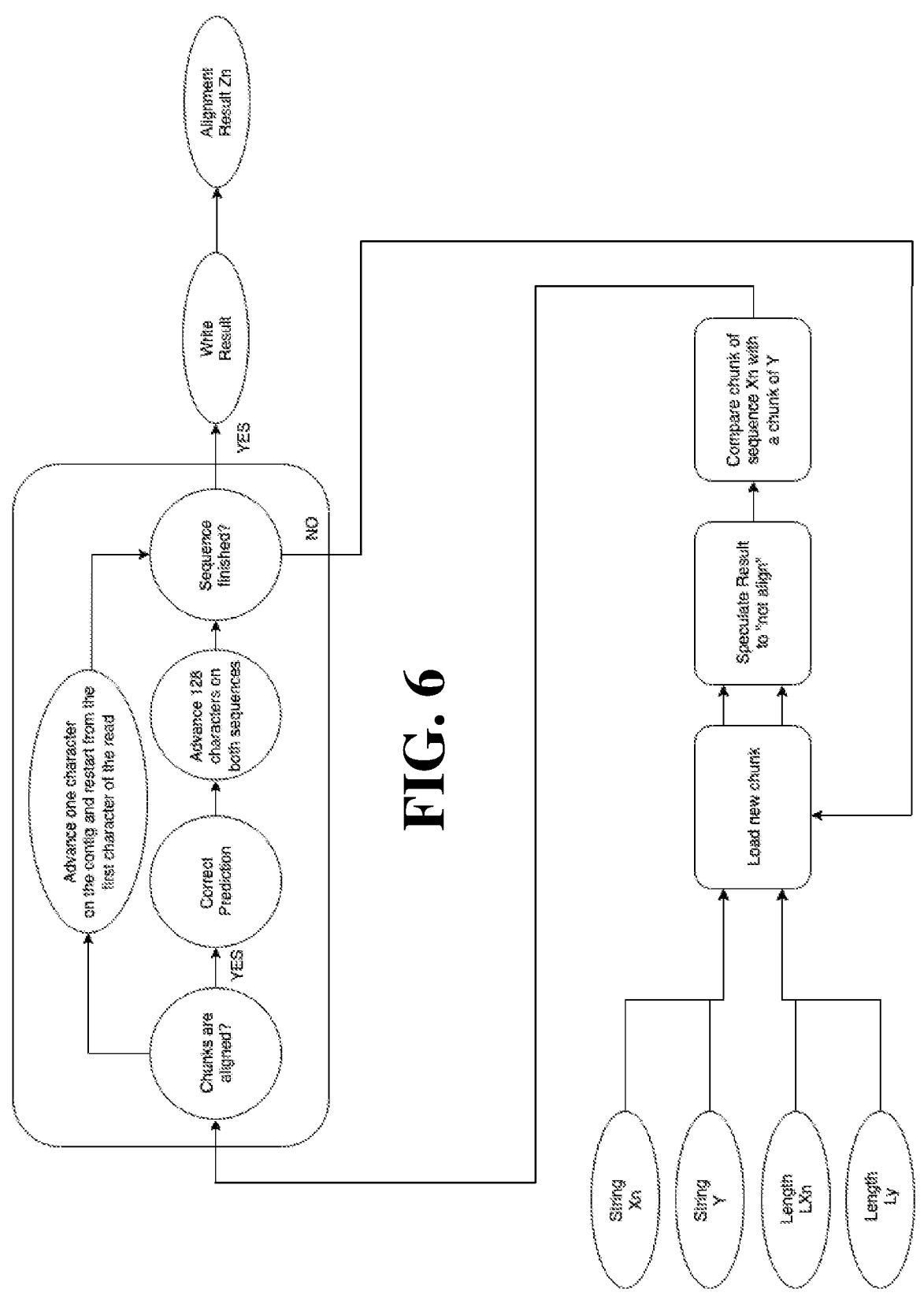
FIG. 6 schematically illustrates operations carried out via hardware for determining whether two strings Xn and Y may be aligned or not.

FIG. 6 conceptually illustrates operations a Finite State Machine (FSM) that compares two strings Xn and Y of characters to determine whether they may be aligned or not. Each sequence in Xn is identified using its length and extracted from X in the first stage of the FSM. Then the speculation module speculates the result of the alignment of the two strings. The comparison between a chunk (block) of characters of the two strings follows. If the two chunks (blocks) are identical, the next state of the FSM fixes the result of a wrong prediction, otherwise a new comparison is scheduled, starting from a character after the previous one. Two strings are considered aligned only when all the blocks of the shorter one are found in the longer one, otherwise the result of the two strings, Zn, is set to "not aligned". This process is repeated for each first string Xn.

The strings Xn and Y are compared an alignment result Zn is generated. Given that two strings have a much higher probability to not to be aligned than to be aligned, and this probability increases as the length of both strings increases, is it initially assumed that the two strings are not aligned. Then a first chunk (block) of the first string (read) of characters and a second chunk (block) of the second string (contig) of characters are compared, wherein the first block and said second block comprise an equal number of characters.

If the blocks are aligned, then the prediction "not aligned" is corrected and a new chunk of the first string and a new chunk of the second string are considered. Merely as an example, if the chunks (blocks) are composed of 128 characters, a new first block and a new second block are selected by considering the successive block of 128 characters.

If the blocks are not aligned, then a new block of the second string (contig) is considered. Preferably the new block of the second string (contig) has the same length of the previously considered second block and it begins in correspondence of the character that followed the start character of the previously considered second block.

When the whole second string (contig) has been considered, a result Zn of the comparison is written into a memory.

The above procedure is repeated for all reads, thus obtaining alignment result data Zn.

Figure 7:
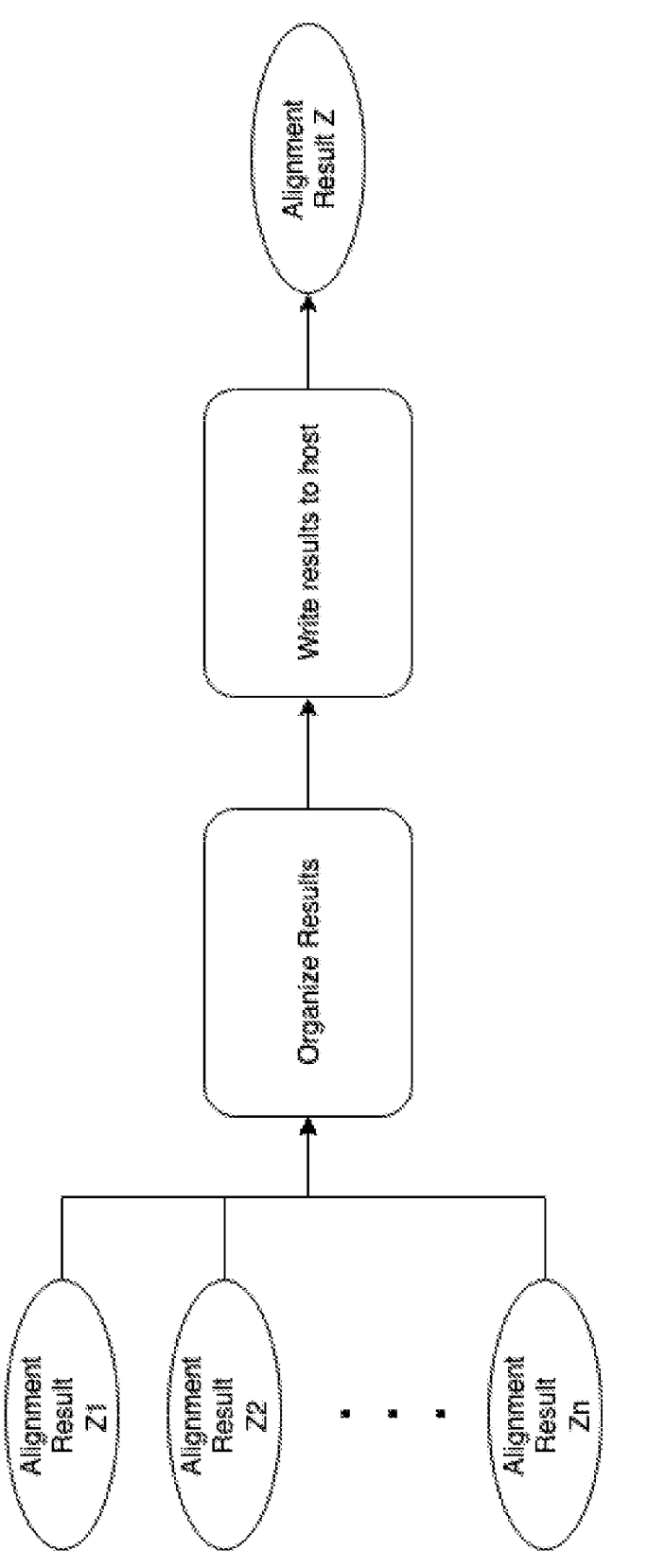
FIG. 7 schematically illustrates how results of alignment generated via hardware are organized to be output.

When all first strings Xn (reads) have been processed, the alignment result data Zn are processed (FIG. 7) and output data Z that contain information about the alignment of the processed first string (read) are written to the host.

The advantages of the disclosed method are:

The possibility of having a highly parallel, energy efficient and scalable, single and multi core, architecture to perform exact matching on FPGA, using a speculation module for the alignment;

The possibility to manage alignments using contigs/reads of any size and length, making the implementation usable in different scenarios.

The part of the processor that performs the alignment has been modeled as a four-stage FSM (Finite State Machine) that includes a speculation module to linearise execution. Finite State Machines are structures that are known to perform well on FPGA [17].

1) The speculation module: To obtain better performance while maintaining a linear execution, we developed a speculation module inside the FSM. This module relies on the fact that two sequences have a much higher probability to not be aligned than to be aligned; this probability increases as the length of both the sequences increases. This means that contigs will likely not align with the read they are compared against. Because of this, we suppose that two sequences will never align. We apply this speculation by predicting the result of each alignment. Every time a new alignment starts, the FSM sets its result as not aligned. The FSM reads data and it immediately sets itself to load different sequences to compare the next cycle as the alignment will not happen. To fix the result in case of a wrong prediction, the FSM always saves data regarding the current alignment position. Indeed if an alignment does occur, the architecture changes its predictions to adapt to this event in the following cycles. The FSM fixes every index that was set ahead by loading the cached information and the correct data is loaded in the next cycles. By doing this, the pipeline does not need to be flushed every time an alignment occurs, but it continues its execution normally.

Figure 8:
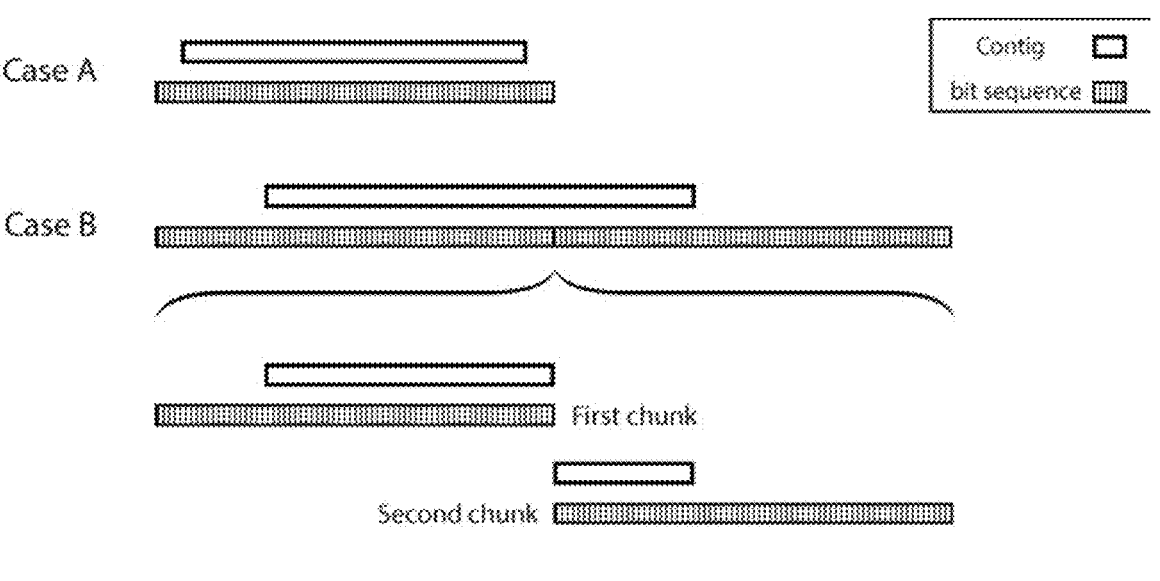
FIG. 8 illustrates the fact that contigs can start in every position of the 512-bit chunk. Case A: the contig is entirely contained in one chunk. Case B: the sequence is placed between two chunks, so it is necessary to load both chunks for storing the entire sequence.
Figure 9:
FIG. 9 illustrates the fact that read block and contig block can have different lengths. Case A: reads and contig have the same lengths. Case B: reads and contig do not have the same lengths, so a set of NULL character is added in the tail of the sequence.
Figure 10:
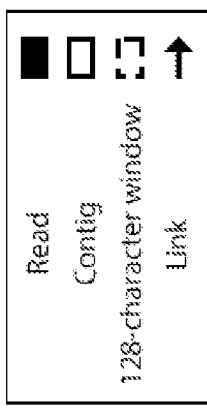
FIG. 10 illustrates a read with length higher than 128 characters is compared using the window approach. The windows are linked to each other to provide a complete comparison.
Figure 10:
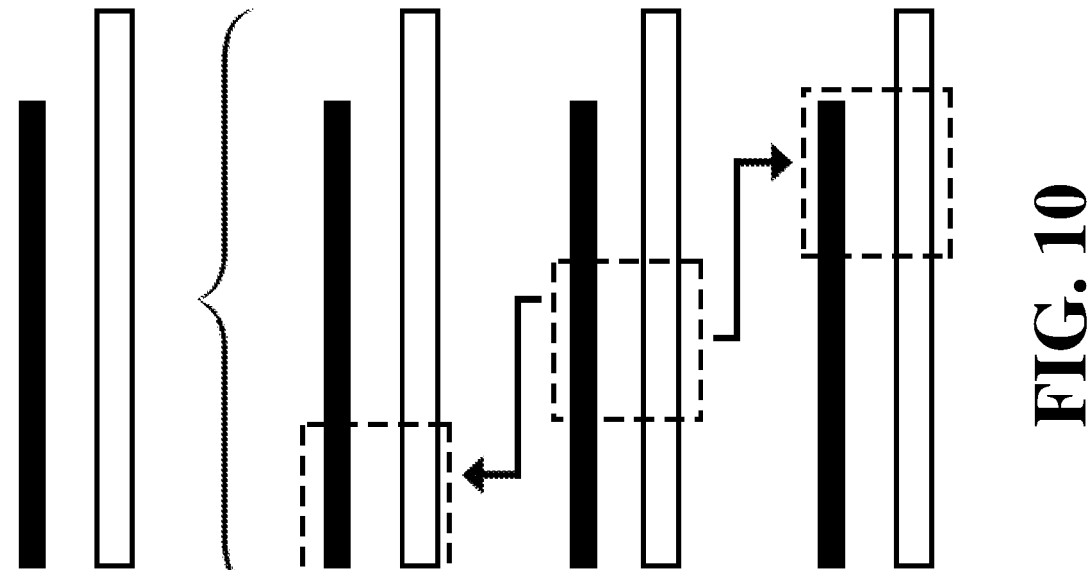
Figure 11:
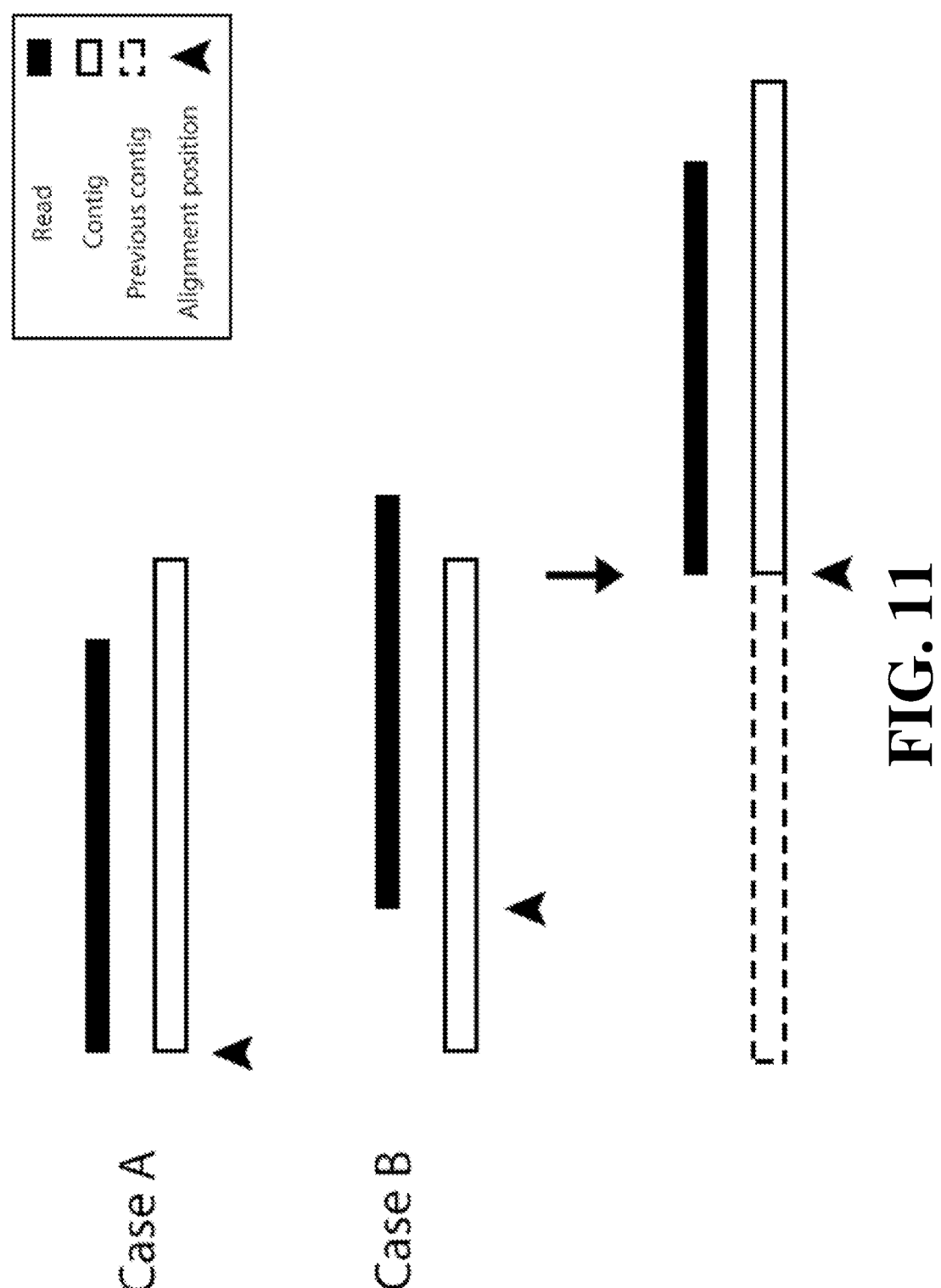
FIG. 11 illustrates read and contig being compared. Case A: alignment position and read length do not exceed the contig length. Case B: alignment position and read length exceed the contig length, thus the comparison will be performed using the next contig.

2) The circular Finite State Machine (FSM) for sequence alignment: Since the FSM does not need to have divergent paths, we modeled it as circular, where each state has only one previous and one following state. The core iteratively fetches a read sequence and compares it against all the contigs in the local BRAM buffers. The main issue with this type of computation lies in the load of different contigs in case of a mismatch. In fact, while the read remains fixed, a new contig needs to be fetched. These sequences, however, have been stored as consecutive elements in the local memory, making it difficult to understand when a new contig starts. A new contig could start in the middle of a 512 bits block, or it could be spread across different memory blocks (FIG. 8). To solve this issue, a specific state of the FSM fetches and organizes data before the comparison phase. The loading state always fetches two consecutive contig blocks and creates a single block of 128 characters with only the information needed. The FSM then compares the newly obtained block and the block that contains read characters. The read block could be shorter than the contig block if the two sequences are not the same length. In this case, only the part that contains characters is compared, as the read is loaded with NULL characters after the valid ones as seen in FIG. 9, case B. After the comparison state, the architecture checks if there is a misalignment. If there is an error, nothing has to change, because the architecture already predicted that the two sequences would not align. Otherwise, information regarding to the position of the alignment and the contig identifier are loaded from the cached data and the prediction of the alignment is updated. When sequences are longer than 128 characters every comparison is correlated with the previous one and the following one (FIG. 10). If a mismatch occurs, the correlation breaks as the speculation was right. Otherwise, this correlation remains intact, the position of the alignment remains the same until there is a misalignment or the processor reaches the end of the sequences. By doing this, we are able to compare sequences of any length, while maintaining a small window for the comparison. If the read is completely aligned, a flag tells the core not to search for another alignment for that particular contig. To reduce the number of comparisons needed for every contig, our architecture also performs a feasibility check on the alignment position by controlling the sizes of the two string pairs (FIG. 11). This cycle of loading, updating, comparing and saving results is repeated until there are no contigs left to compare. Then, the results of the alignments are sent back to the host and the core is available to fetch new data.

C. Multicore

Figure 12:
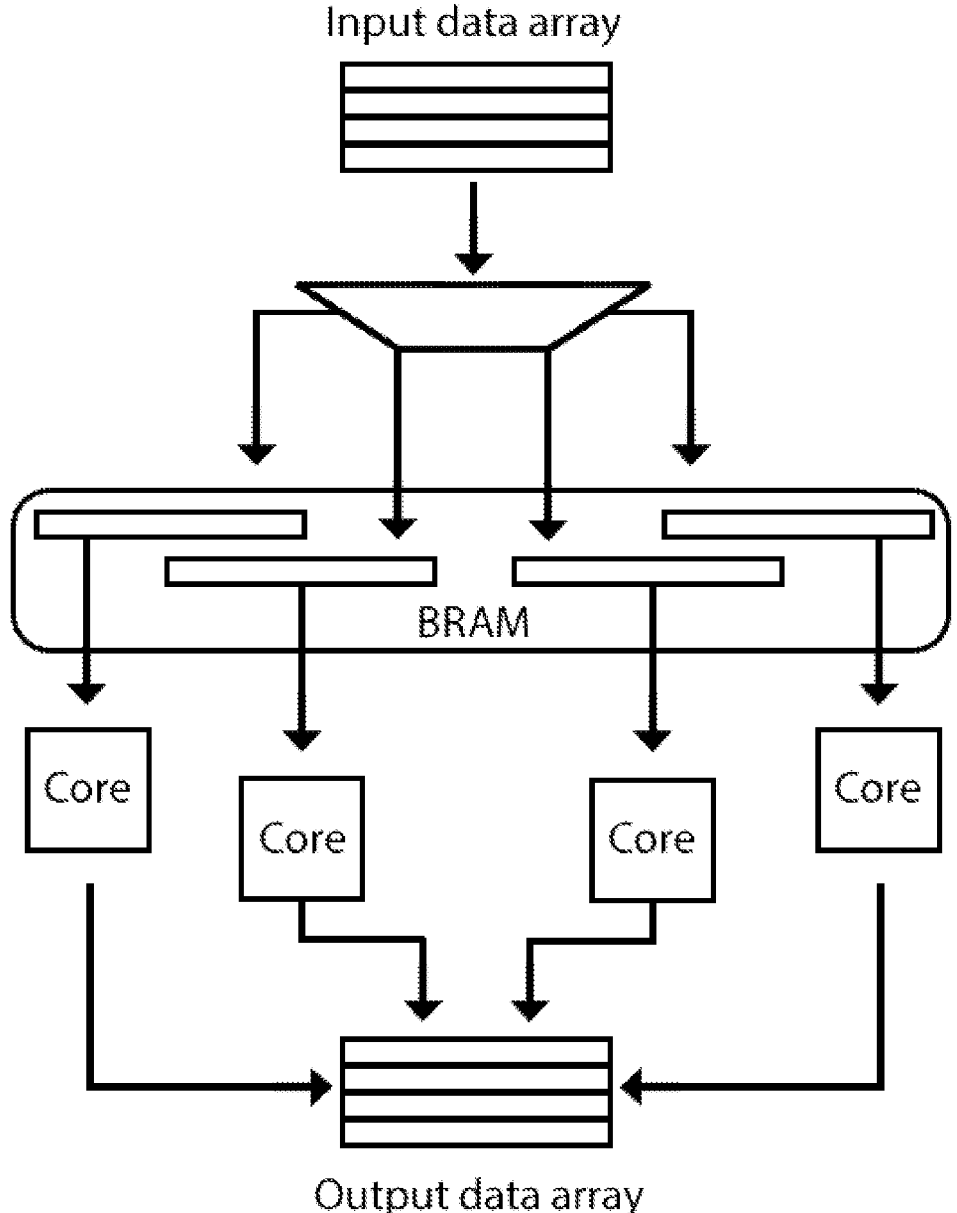
FIG. 12 illustrates a multicore architecture. A dispatcher takes the input array and stores it in four separate arrays in the BRAM. Each core processes a single array. Finally, the results are placed in the output array.

The design we described so far permits an easy replication. Each core in fact, is independent and capable of processing different read/contig pairs in parallel. To obtain better results with our implementation and make better use of the available resources on the FPGA, the design has been replicated into a multicore architecture. The structure of the single processor FSM remains the same, but now data is fetched differently (FIG. 12). The multicore architecture is composed by four or eight cores, according to the target board, and a data dispatcher to distribute data. In this multicore implementation, a single array of data contains all the information regarding the different sequences. It is up to the dispatcher to read this array and organize it into multiple buffers, one per each core. Furthermore, when the FPGA offers more than a memory port, the data reader can read multiple sequences in parallel. Similarly, the core writes output data on the same exact memory port it read the input data. This allows to schedule read and write operation for each core independently, permitting to scale performance linearly with the number of cores and available memory ports. Each core is totally independent to the others, indeed multiple reads can be aligned with multiple contigs, or one sequence can be maintained fix while changing the others. A description of the architecture can be found in FIG. 12. We have implemented 4 cores on the Alpha-Data board and we instantiated 4 and 8 cores on the Alveo U200 board as this board has more resources available.

A. Experimental Settings

The design of the architecture has been described using C++ and Xilinx Vivado HLS. Xilinx SDAccel has been used to perform the bitstream generation step. SDAccel also takes care of the runtime of the application. The host code of the application has been done using OpenCL and the communication between host and FPGA device is performed using the OpenCL APIs. SDAccel requires that the communication among the devices happens respecting the OpenCL memory hierarchy. The latter expects a global memory shared among host and device, and a local and private memory located on the device itself. The device is connected to the host computer through PCI Express. The architecture has been a peak frequency of 3.6 GHz, and has been executed using the same settings provided by SSPACE. Bowtie runs using a single core, as SSPACE permits only to run the alignment step of Bowtie in parallel, which takes only 0.6% of the total execution time, while the BWT construction is always executed using a single core. We also compared our design against an optimized software version of the exact alignment algorithm without the BWT structure. To leverage all the cores available in our server we optimized this software using OpenMP to distribute its load on 40 threads, and then we compiled and run it on the same server as Bowtie, using the 03 optimizations. For what concerns the power efficiency, we have calculated it using the formula:

$$PowerEfficiency\left[\frac{min^{-1}}{W}\right] = \frac{\frac{1}{ExecutionTime}}{PowerConsumption} \tag{1}$$

For the power consumption of the Intel Xeon, we have used 230 W as described in [18], while for the Alpha Data board we used a reference value of 25 W as indicated in [7]. Finally, for the Alveo board, we used a reference value of 23:9 W that we have benchmarked using xbutil, a tool provided within SDAccel 2018.2. To test both the hardware and the software version, we used a dataset of 10 million contigs long 128 characters and 2 thousand reads sized 128 base pairs, a typical input for SSPACE. Then, we tested the hardware version of the aligner increasing the size of the input to demonstrate the scalability capabilities of our architecture.

B. Experimental Results

Table 1 shows the execution times for the softwares analyzed, as well as the results obtained by our hardware architecture, and provides a comparison among software version of the alignment application and the hardware one.

TABLE I

Execution times of Bowtie, the Exact Alignment algorithm (without BWT) in software and the Exact Alignment algorithm on FPGA with 10M contigs and 2 k reads both of length 128 characters coming from a human genome

| Application | Platform | No. Cores | Exe. Time (min) | Speedup w.r.t. Bowtie | Speedup w.r.t. Exact Align. | Power Eff. w.r.t. Bowtie | Power Eff. w.r.t. Exact Align. |
|---|---|---|---|---|---|---|---|
| Bowtie (BWT & Alignment) | CPU | 1 | 137.00 | 1.00x | — | 1.00x | — |
| Exact Alignment (no BWT) | CPU | 40 | 4.10 | 34.25x | 1.00x | 31.70x | 1.00x |
| Alpha Data ADM-PCIE-7V3 | FPGA | 1 | 21.51 | 6.36x | 0.18x | 55.60x | 1.25x |
| | FPGA | 4 | 6.73 | 20.35x | 0.59x | 177.71x | 5.60x |
| Alvero U200 | FPGA | 1 | 13.93 | 9.83x | 0.28x | 89.80x | 2.83x |
| | FPGA | 4 | 3.59 | 38.21x | 1.11x | 348.48x | 10.99x |
| | FPGA | 8 | 1.81 | 75.86x | 2.20x | 691.18x | 21.80x | benchmarked using the OpenCL events that provide an easy to use API to profile the code that runs on the FPGA device. The final design has been benchmarked on two platforms, both equipped with a Xilinx FPGA. The first platform is an Alpha-Data ADMPCIE-7V3 powered by a Virtex-7 FPGA and the second one is a Xilinx Alveo U200 powered by an UltraScale+ XCU200 FPGA. For the first platform, we used the 2017.2 edition of the tool, while for the second one we used the 2018.2 xdf edition. The first platform has been tested on a local server with 8 GB of RAM and an Intel i7 processor while the second one has been tested on the Nimbix Cloud computing platform. The software version of Bowtie has been compiled and run on a local server with 380 GB of RAM and an Intel Xeon E5 2680 v2 processor with For all the tests we used a typical input composed of 10M contigs and 2k reads both of length 128 characters. The first column of the table identifies the application, the second one expresses the platform where the applications have been tested and the third column states the number of cores. The fourth column reports the execution time in minutes and the following two columns show the speedups over the software version of Bowtie and the software version of our aligner that does not exploits the BWT as a support structure for the alignment. Finally, the last two columns show the increment in terms of power efficiency of all the implementations with relation to the software version of the aligner in SSPACE and with relation to the exact alignment, both run on the Intel Xeon. We can observe a significant speedup over software in the multicore implementation, while the single core outperforms both the software solutions only in power efficiency. The difference between the implementation on the ADM-PCIE7V3 board and the Alveo U200 is that the Alpha Data has only one memory port and achieves a frequency of 200 Mhz, while the Alveo U200 has four memory ports, thus it is able to read data in parallel in the multicore, and achieves a frequency of 300 Mhz. Because of this, the Alveo outperforms the Alpha Data, in particular in the multicore implementation where the Alpha Data board has to wait more time to load the data onto the FPGA because of the single port. Furthermore, we can observe as all the implementations on FPGA show a significant increment with respect to the implementations on the Intel Xeon in terms of power efficiency, reaching an improvement of more than 600 and 20 times when considering the best implementation on the Xilinx Alveo U200. Considering previous work on the same topic, FHAST [16] accelerates Bowtie on FPGA. However, we do not think is fair to compare it to this implementation as it requires building the BWT in software before using the hardware implementation. In these regards, the portion accelerated by FHAST is only 0.6% of the total execution of SSPACE, resulting in a little impact on the overall execution of the tool.

As far as our knowledge, the work presented here is the first implementation of the entire Bowtie exact alignment algorithm using FPGA. Furthermore, our implementation performs the alignment directly, with no requirements on the building of the BWT structure prior to execution.

Figure 13:
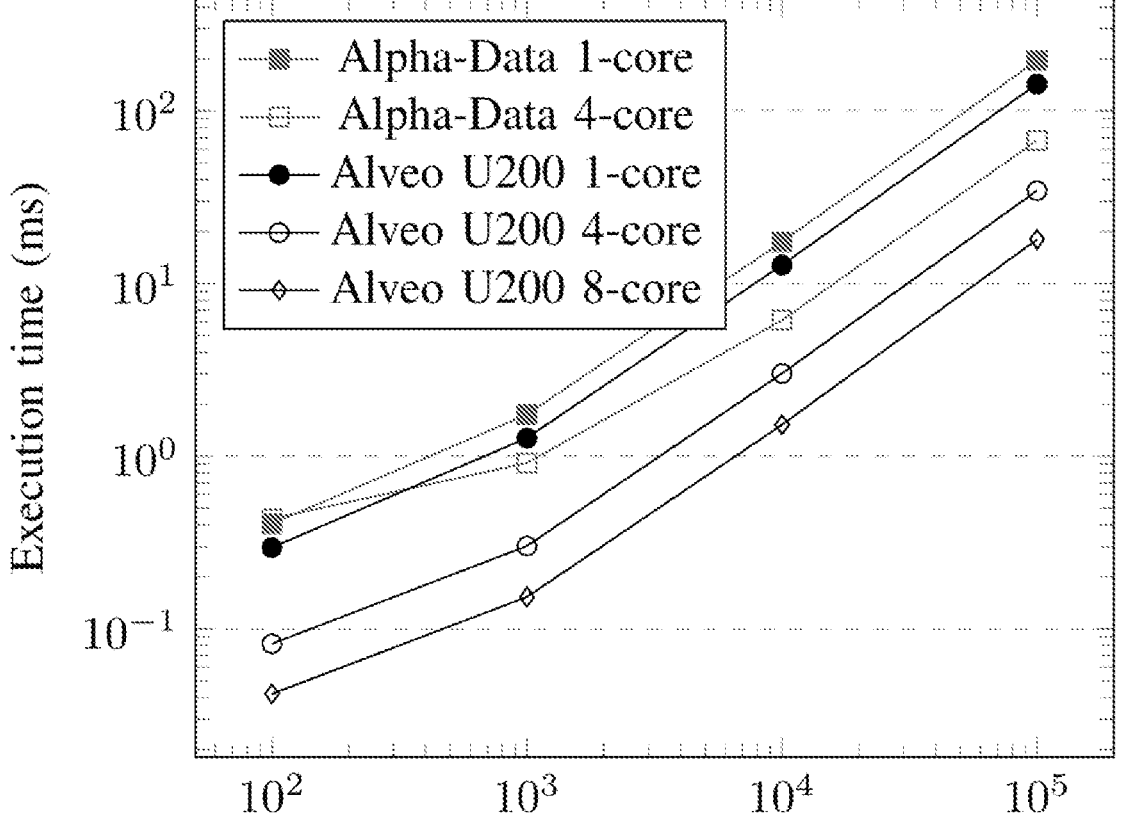
FIG. 13 is a graphical representation of execution times of the alignment on FPGA with 1 k contigs and a single read with inputs of different lengths.

Finally, in FIG. 13, we can see how the execution times scale up when the length of the sequence increases. Multicore execution times are reduced to ⅓ in the case of the Alpha-Data implementation, ¼ and ⅛ in the Alveo implementation with respect to the single core. The reason why the Alpha-Data board does not reduces execution time as the Alveo, is that it is limited to a single port, requiring more time to fetch data. Indeed, this limitation is particularly noticeable using very small datasets as inputs, while is less noticeable when using bigger datasets, as much of the execution time is now spent comparing the sequences and not by loading them. Our implementation offers a significant speedup over the overall execution of the Bowtie tool while also maintaining the flexibility of the software to align sequences of different lengths. It is also important to notice that our architecture is not bounded to the scaffolding process. In fact, it is possible to reuse such architecture to all the tools that integrate Bowtie as exact aligner.

A design of an architecture implemented on FPGA to accelerate the algorithm of exact string matching used by Bowtie has been presented. We explained its application into de-novo genome assembly, in particular with the SSPACE tool and how we optimized the algorithm. We have proposed and described the implementation of a single core architecture based on a FSM. Then, we have demonstrated how our architecture is capable of scaling in performance linearly with the number of cores when implementing its multicore version. The final architectures achieves remarkable results providing: a speedup of 75.86× for the multicore implementation and a speedup of 9.83× for the single core with respect to Bowtie; a speedup of 2.2× for the multicore implementation and a speedup of 1.11× for the single core with respect to the optimized software implementation of the alignment algorithm and, finally an increment in power efficiency up to more than 600, and more than 20 times when compared to the software versions of Bowtie and the exact alignment algorithm. These results would also speedup the SSPACE tool considerably, knowing that Bowtie takes 86.7% of its execution time. To increase the throughput of this architecture, future implementations will explore new memory organizations. Better throughput could in fact be achieved by streaming data directly to the cores while performing the alignment. The same approach could be used to write the results back to the host, as it will consequently reduce the time spent on writing data. These approaches will permit to continuously read and write data while it is being executed and reduce the number of times the host needs to transfer data to the FPGA. Furthermore, it is possible to integrate the above described implementation within SSPACE to speedup the entire tool.

REFERENCES

[1] A. Bubnoff, "Next-generation sequencing: The race is on," Cell, vol. 132, March 2008.

[2] W. Zhang, J. Chen, Y. Yang, Y. Tang, J. Shang, and B. Shen, "A practical comparison of de novo genome assembly software tools for next-generation sequencing technologies," PloS one, vol. 6, no. 3, 2011.

[3] R. Luo, B. Liu, Y. Xie et al., "Soapdenovo2: an empirically improved memory-efficient short-read de novo assembler," Gigascience, December 2012.

[4] J. T. Simpson, K. Wong, S. D. Jackman, J. E. Schein, S. J. Jones, and B. I., "Abyss: a parallel assembler for short read sequence data," Genome Res, vol. 19, no. 6, pp. 1117-1123, 2009.

[5] M. Boetzer, C. V. Henkel, H. J. Jansen, D. Butler, and W. Pirovano, "Scaffolding pre-assembled contigs using sspace," Bioinformatics, vol. 27, no. 4, pp. 578-579, February 2011. [Online].

[6] D. Sampietro, C. Crippa, L. Di Tucci, E. Del Sozzo, and M. Santambrogio, "Fpga-based pairhmm forward algorithm for dna variant calling," July 2018, pp. 1-8.

[7] L. D. Tucci, K. O'Brien, M. Blott, and M. D. Santambrogio, "Architectural optimizations for high performance and energy efficient smithwaterman implementation on fpgas using opencl," in Design, Automation Test in Europe Conference Exhibition (DATE), March 2017, pp. 716-721.

[8] B. Langmead and S. L. Salzberg, "Fast gapped-read alignment with bowtie 2," Nature methods, vol. 9, no. 4, p. 357, 2012.

[9] L. Warren, G. G. Sutton, S. J. M. Jones, Robert, and A. Holt, "Assembling millions of short dna sequences using ssake," Bioinformatics, vol. 23, no. 4, pp. 500-501, February 2007.

[10] B. e. a. Langmead, "Ultrafast and memory-efficient alignment of short dna sequences to the human genome."

[11] M. Scholz, "N50 statistics." [Online].

[12] P. M. Koren S, Treangen T J, "Bambus 2: scaffolding metagenomes," Bioinformatics, vol. 27, 2011. [Online].

[12] P. M. Koren S, Treangen T J, "Bambus 2: scaffolding metagenomes," Bioinformatics, vol. 27, 2011. [Online]. Available: https://www.ncbi.nlm.nih.gov/pubmed/21926123

[13] A. Swiercz, W. Frohmberg, M. Kierzynka, P. Wojciechowski, P. Zurkowski, J. Badura, A. Laskowski, M. Kasprzak, and J. Blazewicz, "Grasshopper an algorithm for de novo assembly based on gpu alignments," vol. 16, 2018.

[14] S. C. Varma, K. Paul, and M. Balakrishnan, "High level design approach to accelerate de novo genome assembly using fpgas," Digital System Design (DSD), no. 17, pp. 66-73, 2014.

[15] D. D'Agostino, A. Clematis, A. Guffanti, L. Milanesi, and I. Merelli, "A cuda-based implementation of the ssake genomics application," in 2012 20th Euromicro International Conference on Parallel, Distributed and Network-based Processing, February 2012, pp. 612-616.

[16] E. B. Fernandez, J. Villarreal, S. Lonardi, and W. A. Najjar, "Fhast: Fpga-based acceleration of bowtie in hardware," IEEE/ACM Transactions on Computational Biology and Bioinformatics, vol. 12, no. 5, pp. 973-981, September 2015.

[17] A. Comodi, D. Conficconi, A. Scolari, and M. D. Santambrogio, "Tirex: Tiled regular expression matching architecture," IEEE International Parallel and Distributed Processing Symposium, May 2018.

[18] "Intel xeon processor e5-2680 v2,".

The invention claimed is:

1. A method of aligning a first string (read) of characters representing genomic data to a second string (contig) of characters representing genomic data, using at least a pipelined Finite State Machine and a storage memory, the method comprising the steps of:

providing a FPGA or an ASIC configured to implement said Finite State Machine, wherein said storage memory is an internal memory of said FPGA or ASIC;

loading into said storage memory said first string (read) of characters representing genomic data;

loading into said storage memory said second string (contig) of characters representing genomic data;

carrying out cyclically the following steps using said Finite State Machine until all characters of said first string (read) have been compared:

first state: selecting a first block of consecutive characters of said first string (read) of characters and a second block of consecutive characters of said second string (contig) of characters to be compared, said first block and said second block comprising an equal number of characters, a start position of said first block being identified by a first index and a start position of said second block being identified by a second index, second state: determining new values for said second index and for said first index to be used at a successive cycle assuming that the first block of consecutive characters of said first string (read) and the second block of consecutive characters of said second string (contig) do not align, third state: comparing in parallel characters of said first block, identified by said first index identified in first state, of consecutive characters of the first string (read) with corresponding characters of said second block, identified by said second index identified in first state, of consecutive characters of the second string (contig), fourth state: evaluating the result of the comparison performed at third state so that:

1) if the first block, identified by said first index identified in first state, of consecutive characters of the first string (read) and the second block, identified by said second index identified in first state, of consecutive characters of the second string (contig) do not align, returning at first state using the index identified at second state;

2) If the first block, identified by said first index identified in first state, of consecutive characters of the first string (read) and the second block, identified by said second index identified in first state, of consecutive characters of the second string (contig) align, the indexes of said first block and said second block identified at second state are discarded and new indexes are calculated, then returning at first state using the indexes calculated during the fourth state;

3) The comparison ends when either all blocks of the first string (read) successfully aligned to an equal number of blocks of the second string (contig), storing the results into said storage memory, or when there is no match of all blocks of the first string (read) with an any possible sequence of equivalent number of contiguous blocks of second string (contig), storing the results into said storage memory.

2. The method of claim 1, comprising the step of loading into said storage memory a plurality of different first strings (read) into said memory and carrying out the steps of claim 1 for each first string (read) of said plurality of different first string (read).

3. The method of claim 2, comprising the preliminary steps of:

providing to said Finite State Machine input data comprising: a first "read" string of characters representing a plurality of first strings (read) together, a second "contig" string of characters representing a plurality of second strings (contig) together, a first array of integers that contains lengths of said plurality of first strings (read), a second array of integers that contains lengths of said plurality of second strings (contig);

fetching said input data and generating said plurality of different first strings (read) and of said second strings (contig) to be loaded into said storage memory.

4. The method of claim 1, comprising the step of representing each character of said first string (read) and of said second string (contig) with 4 bits into said storage memory.

5. The method of claim 1, wherein said second string (contig) is longer than said first string (read).

6. A hardware device for aligning a first string (read) of characters representing genomic data to a second string (contig) of characters representing genomic data, said hardware device comprising:

a storage memory configured to store said first string (read) and said second string (contig);

a Finite State Machine configured to carry out the method steps of claim 1, wherein said Finite State Machine is implemented in a FPGA or an ASIC and said storage memory is an internal memory of said FPGA or ASIC.

7. The hardware device of claim 6, comprising a plurality of Finite State Machine identical with said Finite State Machine, configured to carry out in parallel multiple instances of the method steps of:

loading into said storage memory said first string (read) of characters representing genomic data;

loading into said storage memory said second string (contig) of characters representing genomic data;

carrying out cyclically the following steps using said Finite State Machine until all characters of said first string (read) have been compared:

first state: selecting a first block of consecutive characters of said first string (read) of characters and a second block of consecutive characters of said second string (contig) of characters to be compared, said first block and said second block comprising an equal number of characters, a start position of said first block being identified by a first index and a start position of said second block being identified by a second index, second state: determining new values for said second index and for said first index to be used at a successive cycle assuming that the first block of consecutive characters of said first string (read) and the second block of consecutive characters of said second string (contig) do not align, third state: comparing in parallel characters of said first block, identified by said first index identified in first state, of consecutive characters of the first string (read) with corresponding characters of said second block, identified by said second index identified in first state, of consecutive characters of the second string (contig), fourth state: evaluating the result of the comparison performed at third state so that:

1) If the first block, identified by said first index identified in first state, of consecutive characters of the first string (read) and the second block, identified by said second index identified in first state, of consecutive characters of the second string (contig) do not align, returning at first state using the index identified at second state;

2) If the first block, identified by said first index identified in first state, of consecutive characters of the first string (read) and the second block, identified by said second index identified in first state, of consecutive characters of the second string (contig) align, the indexes of said first block and said second block identified at second state are discarded and new indexes are calculated, then returning at first state using the indexes calculated during the fourth state;

3) The comparison ends when either all blocks of the first string (read) successfully aligned to an equal number of blocks of the second string (contig), storing the results into said storage memory, or when there is no match of all blocks of the first string (read) with an any possible sequence of equivalent number of contiguous blocks of second string (contig), storing the results into said storage memory.

\* \* \* \* \*